(12) United States Patent
Shaw et al.

(10) Patent No.: US 10,978,180 B1
(45) Date of Patent: Apr. 13, 2021

(54) ENABLING DATA FLOW IN AN ELECTRONIC REFERRAL NETWORK

(71) Applicant: IQVIA Inc., Danbury, CT (US)

(72) Inventors: Katie Shaw, Apex, NC (US); Davie Yang, Morrisville, NC (US); Leonard Bishop, Fuquay-Varina, NC (US); Kimberly Ray, Atlanta, GA (US); Timothy Riely, Raleigh, NC (US); Lucas Glass, Devon, PA (US); Patrick Lample, Paris (FR); Susan Warne, Houston, TX (US)

(73) Assignee: IQVIA Inc., Parsippany, NJ (US)

( * ) Notice: Subject to any disclaimer, the term of this patent is extended or adjusted under 35 U.S.C. 154(b) by 268 days.

(21) Appl. No.: 16/048,845

(22) Filed: Jul. 30, 2018

(51) Int. Cl.
*G16H 10/20* (2018.01)
*G16H 10/60* (2018.01)

(52) U.S. Cl.
CPC ............ *G16H 10/20* (2018.01); *G16H 10/60* (2018.01)

(58) Field of Classification Search
CPC .................................................. G16H 10/20
See application file for complete search history.

(56) References Cited

U.S. PATENT DOCUMENTS

| | | | |
|---|---|---|---|
| 7,401,028 B2 | 7/2008 | Deakter | |
| 9,460,400 B2 | 10/2016 | De Bruin | |
| 2003/0065669 A1* | 4/2003 | Kahn | ............... G06Q 10/10 |
| 2004/0078216 A1 | 4/2004 | Toto | |
| 2004/0243439 A1 | 12/2004 | Huggard | |
| 2005/0071189 A1 | 3/2005 | Blake et al. | |
| 2005/0182663 A1 | 8/2005 | Abraham-Fuchs | |
| 2005/0234740 A1 | 10/2005 | Krishnan et al. | |
| 2006/0080146 A1 | 4/2006 | Cook | |
| 2008/0010254 A1* | 1/2008 | Settimi | ............... G16H 70/00 |
| 2009/0313045 A1* | 12/2009 | Boyce | ............... G16H 10/20 |
| | | | 705/3 |
| 2010/0088245 A1* | 4/2010 | Harrison | ............... G06Q 50/22 |
| | | | 705/317 |
| 2010/0332258 A1 | 12/2010 | Dahlke et al. | |
| 2011/0301982 A1* | 12/2011 | Green, Jr. | ............. G06Q 10/06 |
| | | | 705/3 |
| 2012/0158420 A1 | 6/2012 | Lacal | |
| 2012/0296662 A1 | 11/2012 | Bailey | |
| 2013/0096942 A1 | 4/2013 | Bowles et al. | |

(Continued)

*Primary Examiner* — Michael Tomaszewski
*Assistant Examiner* — Jay M. Patel
(74) *Attorney, Agent, or Firm* — Fish & Richardson P.C.

(57) ABSTRACT

Methods, systems, and apparatus, including computer programs encoded on a computer storage medium, for a computing system that identifies information about a trial program. The information is related to healthcare data for a subset of providers. The system identifies a provider based on analysis of the information and the healthcare data and provides trial program criteria for analysis at a provider system. The provider system has access to healthcare data for subjects that interact with the provider. The computing system generates data indicating a result of screening each subject by analyzing the trial program criteria against healthcare data for each subject and receives data for a selection of a subject from the provider system. The selection is determined using screening data for the subject. A referral network of the system provides the screening data for access and analysis at an investigator system.

20 Claims, 5 Drawing Sheets

(56) References Cited

U.S. PATENT DOCUMENTS

| | | |
|---|---|---|
| 2013/0332190 A1* | 12/2013 | Hoffman ................ G16H 10/20 |
| | | 705/3 |
| 2013/0332191 A1 | 12/2013 | Hoffman et al. |
| 2013/0346104 A1* | 12/2013 | Pillai ...................... G16H 10/60 |
| | | 705/3 |
| 2014/0046926 A1* | 2/2014 | Walton ................ G06F 16/9535 |
| | | 707/710 |
| 2014/0136237 A1 | 5/2014 | Anderson et al. |
| 2014/0236623 A1* | 8/2014 | Shiovitz ................ G16H 10/20 |
| | | 705/2 |
| 2014/0244309 A1 | 8/2014 | Francois |
| 2014/0316793 A1* | 10/2014 | Pruit ...................... G16H 10/20 |
| | | 705/2 |
| 2015/0161336 A1* | 6/2015 | Kalathil ................ G16H 10/20 |
| | | 705/3 |
| 2016/0004820 A1* | 1/2016 | Moore ................ H04L 63/1441 |
| | | 705/3 |
| 2017/0061102 A1* | 3/2017 | Weber ...................... G06F 19/00 |
| 2017/0199189 A1* | 7/2017 | Wade ...................... G16H 50/30 |
| 2018/0119137 A1 | 5/2018 | Matsuguchi et al. |

\* cited by examiner

ENABLING DATA FLOW IN AN ELECTRONIC REFERRAL NETWORK

CROSS-REFERENCE TO RELATED APPLICATION

This application is related to U.S. patent application Ser. No. 15/914,653 filed on Mar. 7, 2018, the contents of which are expressly incorporated by reference in their entirety.

FIELD

This specification relates to predictive computing platforms.

BACKGROUND

As part of the health care process, physicians or other medical care providers may perform clinical trials, programs, and other activities to evaluate the subject safety and efficacy of a pharmaceutical drug or other medical treatment option. The use of health-related trial programs can help to identify novel treatment options for improving overall patient health and reducing health system costs. For the purposes of gaining approval of particular treatment option, a clinical trial or program can be a research study that prospectively assigns human participants/subjects or groups of human subjects to one or more health-related interventions to evaluate the effects on health outcomes.

The effectiveness of a program can depend on the availability of subjects or patients that are suitable for enrollment and participation in the program. Traditional patient or subject enrollment techniques leverage mass media direct to patient campaigns and leverage principal investigators that are responsible for executing the program to recruit patients. However, execution of clinical trials and other controlled programs may be delayed due to challenges in identifying and recruitment of suitable subjects for participation in the program. In some instances, controlled programs are sometimes unable to enroll subjects for participation in the program. In other instances, principal investigators and geographic site locations may miss enrollment targets due to the limited resources for developing and engaging existing subject networks that include suitable subjects for enrollment in a particular program.

SUMMARY

As part of the health care process, physicians or other medical care providers may perform trials, programs, and other activities to evaluate the efficacy of a particular pharmaceutical drug or other medical treatment option. Conducting health-related clinical trials can help to identify medical treatment options for improving overall patient health and reducing health system costs. Clinical trials and other controlled programs are generally conducted by investigators that use a particular geographic site location(s) to interact with study subjects and execute process steps for conducting the program. An investigator, a geographic site location, or both, can form an entity that executes a program. The effectiveness of a program can depend on the availability of subjects or patients that are suitable for enrollment and participation in the program.

In the context of identifying patients for enrollment in a clinical trial program, techniques are described for a predictive platform of a computing system that identifies information about a trial program, where the information is related to healthcare data included in datasets, and identifies an investigator based on the information about the trial program. The system identifies a provider based on analysis of the information and the healthcare data and provides trial program criteria for analysis at a provider system. The provider system has access to healthcare data for subjects that interact with a provider, such as a primary care doctor or a physician that prescribes treatment options to subjects.

The computing system generates data indicating a result of screening each subject based on analysis of the information about the trial. For example, the system analyzes trial criteria specified in the information against healthcare data for each subject. The systems receives data for a selection of a subject from the provider system based on certain outcomes or determinations about the subject that are included in the screening data. The selection is determined using screening data for the subject and indicates whether a subject is a candidate for participation in a clinical trial program. A digital referral network of the system provides the screening data for access and analysis at an investigator system.

One aspect of the subject matter described in this specification can be embodied in a computer-implemented method. The method includes, identifying, by a computing system, information about a trial program, the information being related to healthcare data for a subset of providers; identifying, by the computing system, a provider from among the subset of providers based on analysis of the information about the trial program and the healthcare data for the subset of providers; and providing, by the computing system, the information about the trial program for analysis at a provider system, the provider system being configured to access healthcare data for multiple subjects that interact with the provider.

The method includes generating, using the computing system, data indicating a result of digitally screening each of the multiple subjects based on analysis of the information about the trial program against the healthcare data accessed for each of the multiple subjects; receiving, at the computing system and from the provider system, data for a selection of a subject from among the multiple subjects, the selection being determined at the provider system based on screening data generated for the subject; and providing, using a digital referral network of the computing system and for access at an investigator system, the screening data for the subject, wherein the screening data describes a screening outcome of the subject and is provided for analysis by the trial investigator.

These and other implementations can each optionally include one or more of the following features. For example, in some implementations, the screening data is provided through communication channels enabled by the digital referral network of the computing system based on a referral connection that exists between the identified provider and the trial investigator. In some implementations, the screening data comprises an anonymized identifier for the subject and data describing personal health attributes of the subject; and the screening data is linked to electronic healthcare records and electronic healthcare transaction data about the subject that are derived based on the subject's interaction with the provider. In some implementations, the subject is a prospective candidate for participation in the trial program based on criteria defined by the information about the trial program.

In some implementations, the criteria includes inclusion criteria and exclusion criteria, and the method further includes: processing, using the computing system, the inclusion criteria and the exclusion criteria against information contained in at least one of the electronic healthcare records or the electronic healthcare transaction data about the subject; and in response to the processing, determining, using the computing system, that the subject is a prospective candidate for participation in the trial program.

In some implementations, receiving the data for selection of the subject from the provider system is preceded by the provider system: accessing healthcare data for the multiple subjects that interact with the provider; determining that the subject is a candidate for participation in the trial program based on analysis of data describing a first healthcare indication or a therapeutic compound referenced in the information about the trial program; and in response to determining that the subject is a candidate for participation in the trial program, providing, for receipt at the computing system, a notification that indicates the selection of the subject.

In some implementations, determining that the subject is a candidate for participation in the trial program includes: identifying a second healthcare indication connected to the subject based on the data describing the personal health attributes of the subject; determining a match between the first healthcare indication and the second healthcare indication based on analysis of terms that describe each of the first and second healthcare indications; and based on the determined match, determining that the subject is a candidate for participation in the trial program. In some implementations, determining that the subject is a candidate for participation in the trial program includes: determining that the subject is a candidate for participation in the trial program based on the screening data and the screening outcome.

In some implementations, the screening outcome described by the screening data indicates that the subject passed a pre-screening analysis based on results of an analytical sequence executed using the computing system; or the screening outcome described by the screening data indicates that the subject failed a pre-screening analysis based on results of an analytical sequence executed using the computing system.

In some implementations, providing the information about the trial program includes: determining that a referral connection exists between the identified provider and the trial investigator. In some implementations, determining that the referral connection exists between the identified provider and the trial investigator includes: providing, by the provider system and to the investigator system, a request to establish the referral connection; providing, by the investigator system and to the provider system, reply communication that is responsive to the request; and determining that the referral connection exists between the identified provider and the trial investigator based on information in the reply communication.

Other implementations of this and other aspects include corresponding systems, apparatus, and computer programs, configured to perform the actions of the methods, encoded on computer storage devices. A computing system of one or more computers or hardware circuits can be so configured by virtue of software, firmware, hardware, or a combination of them installed on the system that in operation cause the system to perform the actions. One or more computer programs can be so configured by virtue of having instructions that, when executed by data processing apparatus, cause the apparatus to perform the actions.

The subject matter described in this specification can be implemented to realize one or more of the following advantages. Techniques are described for implementing a referral platform that efficiently and securely analyzes healthcare data and enables referral data to be provided to an investigator system using established referral connections between healthcare providers and investigators that execute trial programs.

A computing platform uses a specific set of computer-implemented rules to analyze and processes data describing controlled programs (e.g., clinical trials). Standardized methods for analyzing the data enable the computing platform to identify a healthcare provider that have an established referral relationship with an investigator for referring candidates as subjects for participation in a trial program. The platform leverages a predictive model that executes inference logic to analyze healthcare attributes of a subject against criteria for a clinical trial. Based on this analysis the system identifies subjects with health attributes matching criteria for certain types of clinical trials. The predictive model continuously analyzes new and existing information about subjects and current clinical trials to improve efficiency and accuracy in identifying subjects that are suitable candidates for participation in a clinical trial.

The described platform enables automation of specific data analytics, e.g., for analyzing a subject's sensitive health data against trial criteria and for generating screening data, that previously could not be performed by computer systems in an efficient manner. The described techniques use machine learning to continuously improve upon a match scoring process thereby enabling the platform to identify providers or physicians that are more likely to refer candidates that are suitable subjects for participation in a particular trial program. A repeatable automated process is provided that involves minimal human intervention and does not require manual execution of business agreements to facilitate sharing a subject's medical data and screening outcomes between providers and trial investigators.

The specific computing rules enable healthcare providers to access a vast array of clinical trial data in order to locate specific trial programs that align with the healthcare needs of their patient base. As such, the described techniques enable a computer to perform operations that the computer was previously unable to perform due to challenges with effectively analyzing trial criteria against a subject's medical data. This analysis enables a computer to automatically and efficiently generate screening data as well as share referral data with screening analysis outcomes between different providers and investigators. The described techniques use pre-established referral connections of a digital referral network to securely exchange sensitive patient screening data between different medical entities. This facilitates subject referrals among entities and enhances or improves relevant technologies relating to efficient identification and enrollment of subjects in clinical trials.

The details of one or more implementations of the subject matter described in this specification are set forth in the accompanying drawings and the description below. Other potential features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
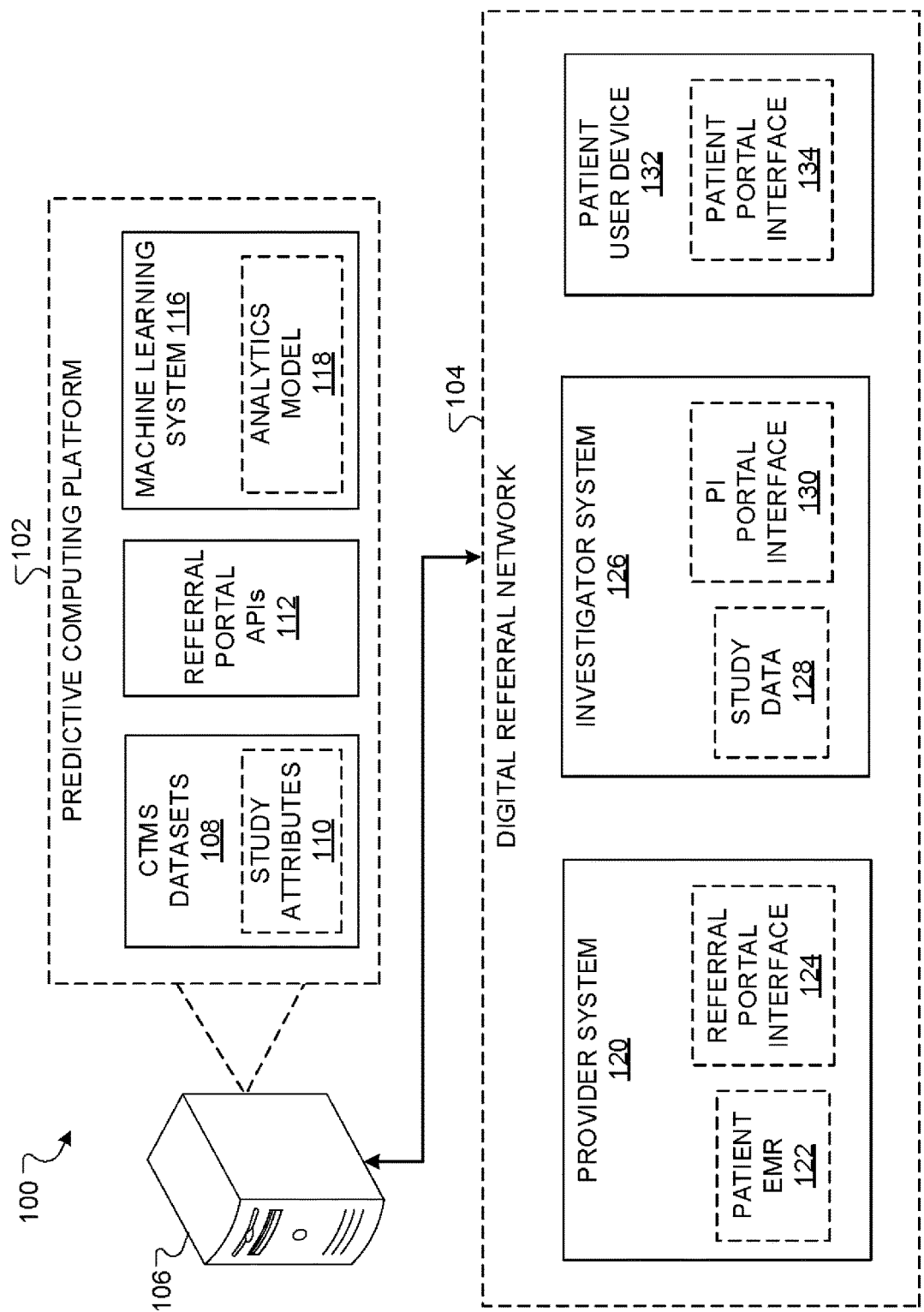
FIG. 1 shows a block diagram of an example computing system that includes a computing platform for enabling data flow in a computer-based referral network.

FIG. 1 shows a block diagram of an example computing system 100 that includes a computing platform 102 for enabling data flow in a computer-based referral network 104. System 100 includes a server 106 that is configured to implement various computing functions of platform 102 that are described herein. Platform 102 can be a predictive computing platform that includes datasets 108, an application interface 112, and a machine learning (ML) system 116. System 100 may further include multiple computers, computing servers, and other computing devices that each include processors or processing devices and memory that stores compute logic or software/computing instructions that are executable by the processors. In some implementations, multiple computers can form a cluster of computing nodes or multiple node clusters that are used to perform the computational and/or machine learning processes described herein.

Server 106 is configured to access each of datasets 108, application interface 112, and ML system 116. In some implementations, ML system 116 and application interface 112 are included within server 106 as a sub-system of hardware circuits including one or more processor microchips. In general, server 106 can include one or more processors, memory, and data storage devices that collectively form one or more computing systems of server 106. Processors of the computing systems process instructions for execution by server 106, including instructions stored in the memory or on the storage device to display graphical information for a graphical user interface (GUI) on a display of, for example, system 100.

Execution of the stored instructions can cause one or more of the actions described herein to be performed by server 106 (or ML system 116). In other implementations, multiple processors may be used, as appropriate, along with multiple memories and types of memory. For example, server 106 may be connected with multiple other computing devices, with each device (e.g., a server bank, groups of servers, modules, or a multi-processor system) performing portions of the actions or operations associated with the various processes or logical flows described in this specification.

Datasets 108 can be stored using one or more storage mediums that store datasets which include information about a variety of different controlled programs. For example, the information can describe entities that execute a variety of different programs (e.g., clinical trials or other controlled programs, including real-world and pragmatic programs). In some implementations, datasets 108 can indicate objectives that have been defined for different trial programs. Information in datasets 108 indicate investigators (and providers) that are appropriately skilled to conduct (or support) trial programs based on a specialty of the entity (or provider) and an experience level of the investigator in conducting certain trial programs.

In some implementations, datasets 108 store information accessed by an example program management system (e.g., a clinical trial management system (CTMS)). For example, datasets 108 can be connected to an example CTMS that interacts with datasets 108 to retrieve, modify, and store information about multiple clinical trial programs. Hence, datasets 108 can include study attributes 110 that provide details about each of the multiple programs. For example, the details can include inclusion criteria specifying conditions for acceptance of a particular patient or subject into a trial program and exclusion criteria specifying conditions for exclusion of a particular patient from participation in a trial program. Datasets 108 can also include information pertaining to healthcare transactions. For example, datasets 108 can include information describing medical specialties of individual providers as well as transaction data describing health related interactions between patients and each of the multiple providers. Datasets 108 can also include information describing one or more connections that exist between investigators, healthcare providers, and public or private institutions (e.g., health care organizations, academic institutions, etc.).

Application (app) interface 112 is configured to facilitate access to various subsets of information included at datasets 108 or platform 102. In some implementations, interface 112 is an example application program interface (API) for accessing a variety of application specific data for generating information displayed at different entity systems and client devices using example graphical interfaces described herein. In general, computing logic of server 106 can include software instructions for one or more APIs (e.g., interface 112) that are associated with data functions of platform 102. The functions include providing data for referring a subject or patient to a trial program, indicating a subject's enrollment status, indicating an investigator's acceptance of a subject, or generating listings of clinical trials and trial program criteria associated with each clinical trial. The software instructions can include sets of coded routines and/or proprietary protocols for receiving, processing, and exchanging data communications between computing platform 102 and each of the one or more systems and client devices of digital referral network 104.

A machine learning (ML) system 116 can be included within server 106 as a sub-system of hardware circuits that are programmed to generate analytics model 118. For example, ML system 116 can include at least one neural network represented by a processor microchip that performs computations for generating learned inferences. Analytics model 118 can be generated based on learned inferences that result from iterative analysis of new and existing information included at datasets 108. For example, model 118 can access information including clinical trial criteria, health attributes of a subject, provider and investigator data, and healthcare transactions at datasets 108. Model 118 access the information to execute certain predictive and analytical processes using the information in order to generate inferences about subjects or providers within referral network 104.

In some implementations, ML system 116 can be a dynamic recommendation engine that uses different sources of information accessed from datasets 108 to model connections between data describing healthcare activity, clinical trial programs, provider research, educational materials, and subject's health attributes. ML system 116 can generate an analytics model 118 that is configured to weight each connection based on the importance of the type of connection and a particular topic of interest. For example, model 118 can identify a topic of interest that corresponds to a trial program (e.g., a diabetes treatment trial) and can weight a connection based on the importance of the type of connection using data for a healthcare provider that specializes in treating patients with diabetes.

Referral network 104 is generally formed by two or more entity client systems, user devices, or combinations of these systems and devices. For example, referral network 104 generally includes a first provider system 120 and a second investigator system 126. In some implementations, referral network 104 also includes a client device 132 for accessing a patient portal interface 134. Each of provider, investigator systems 120, 126 and client device 132 can include any known computer system, such as a desktop computer, a laptop computer, a tablet device, a mobile device, a smartphone, or any other related computing device configured to receive user input, exchange data communications with server 106, or exchange data communications with other computing systems.

Provider system 120 can be a computer system for a healthcare entity, such as a healthcare provider or a treating physician. Provider system 120 can store health data 122 that provides information about individuals that engage in healthcare related transactions with a provider that manages provider system 120. Health data 122 can include information about a variety of different patients, patient populations or patient groupings. In some implementations, assets of health data 122 are patient's electronic medical record (EMR), including EMR data inclusive of lab results, and other types of assets, such as claims data, prescription data, sales data for different treatment options, and lab data for different treatment options.

For example, a patient's EMR can provide a digital or electronic representation of the patient's hardcopy or paper medical chart and can include some or all information about the patient's medical history. In some implementations, health data 122 can include any information related to a patient's overall health, such as one or more medical conditions of the patient, or prescription therapies or pharmaceutical products being used by the patient. Analysis of health data 122 can be used to identify patient populations and other patient characteristics that are suitable candidates for participation in one or more clinical trial programs.

A computer system of provider system 120 can be configured to exchange data communications with platform 102 and investigator system 126, via platform 102. For example, a display device of provider system 120 can generate a referral portal interface 124 that enables a provider to receive communication messages generated by platform 102. As described in more detail below, at least one communication message can include an invitation or request to join referral network 104. Acceptance of the request to join referral network 104 enables a provider to refer one or more patients to an investigator for participation in a trial program. The provider can refer the one or more patients based on a referral connection that is established between the provider and an investigator that are each included in referral network 104.

Investigator system 126 can correspond to a computer system for an entity that manages a program, such as a principal investigator that executes a clinical trial program at a particular geographic site location. Investigator system 126 can store study data 128 that provides information about a clinical trial being executed by an investigator, such as information about patient volumes and other subjects that are tailored to particular study/trial program parameters. In some instances, study data 128 can include information that is similar (e.g., substantially similar) to study attributes 110, except that the information is specific to the clinical trial being executed by the investigator.

A computer system of investigator system 126 can be configured to exchange data communications with platform 102 and with provider system 120, via platform 102. For example, a display device of investigator system 126 can generate an investigator portal interface 130 that enables an investigator to receive communication messages generated by platform 102. At least one communication message can indicate that a provider seeks to establish a referral connection with an investigator that manages investigator system 126. Acceptance of the provider's request by the investigator forms an electronic referral connection that enables the provider to refer one or more patients to the investigator as candidates for participation in a trial program being executed by the investigator. Hence, the provider can refer the one or more patients to the investigator based on the referral connection that is established, via platform 102, between the provider and the investigator that are each connected in referral network 104.

Client device 132 can correspond to a user device or computer system for a subject/patient that is a candidate for participation in a clinical trial or that is currently participating in a trial program at a particular geographic site location. Client device 132 is used by a subject to access one or more patient portal interfaces 134. Portal interface 134 can provide a subject with access to a subset of study data 128. For example, interface 134 can provide limited sets of information about a specific clinical trial being executed by an investigator associated with the subject. The information can identify clinical trials in which the subject is presently participating. In some implementations, interface 134 presents information about a subject's referral status when health attributes of the subject are being evaluated by a provider or an investigator, or both. In some cases, a provider or investigator evaluates screening data that includes the subjects health attributes to determine whether the subject can participate in a clinical trial program.

Portal interface 134 is configured to exchange data communications with platform 102 and with provider system 120, via referral portal API 112. For example, a display of client device 132 can generate portal interface 134 to enable a patient or subject to receive communication messages generated by platform 102. At least one communication message can indicate that a health physician provided referral data that includes information about the subject to an investigator. The referral data is provided using a referral connection established between the health physician and an investigator that manages a clinical trial and that is accepting subjects for enrollment or participation in the clinical trial. In some implementations, interface 134 informs a subject of their acceptance in a trial program when a provider has referred the subject to an investigator as a candidate for participation in the trial program and the investigator validates the subject's acceptance into the trial program.

Figure 2:
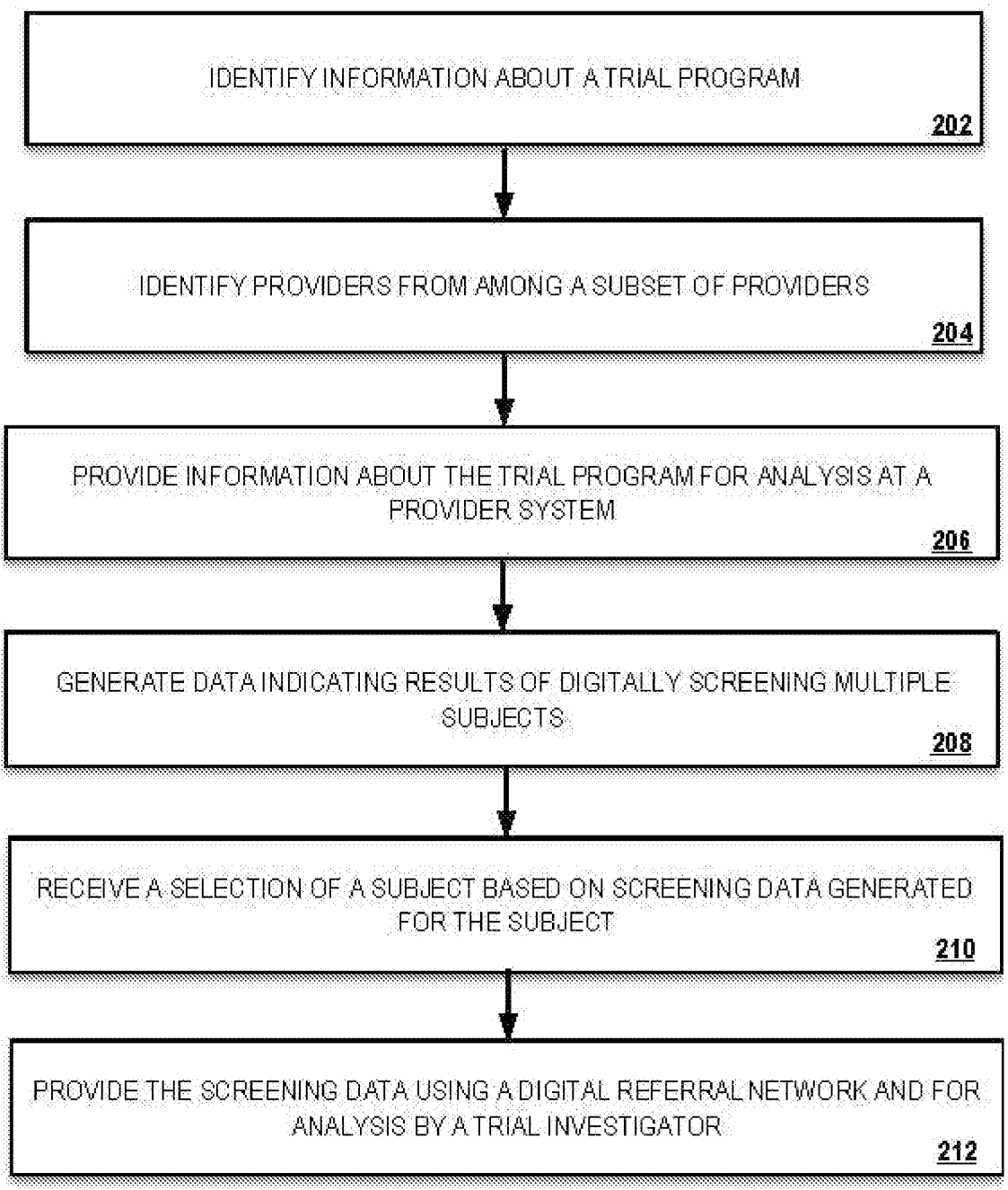
FIG. 2 shows an example process for data exchanges in a digital referral network.

FIG. 2 shows an example process 200 for data exchanges in referral network 104. Process 200 can be implemented or executed using the systems described in this document. Thus, descriptions of process 200 may reference one or more of the above-mentioned computing resources of system 100. In some implementations, steps of process 200 are enabled by programmed instructions that executable by processing devices and memory of the systems described in this document.

Referring now to process 200, system 100 identifies information about a trial program (202). System 100 identifies the information based on analysis of datasets 108. In some implementations, information at datasets 108 that is associated with a clinical trial program is also related to healthcare data for a subset of providers. For example, datasets 108 can include information pertaining to study attributes 110 that provide details about each of a variety of different clinical trial programs. As discussed below, the details can include certain criteria or conditions for accepting, or not accepting, a subject into a trial program. Datasets 108 can also include information pertaining to healthcare transactions. For example, the information describes medical specialties of multiple providers as well as transaction data describing health related interactions between subjects, or patients, and each of the multiple providers. Datasets 108 can also include information describing connections that exist between investigators and healthcare providers, as well as between public or private institutions (e.g., health care organizations, academic institutions, etc.) and a provider and/or investigator. In some implementations, the connections are existing referral connections enabled based on technical features of digital referral network 104.

System 100 identifies a provider from among the subset of providers based on analysis of the information about the trial program and the healthcare data for the subset of providers (204). For example, in response to performing the analysis, system 100 determines that a referral connection exists between a subset of providers and at least one investigator. In some implementations, determining that the referral connection exists between a provider and a trial investigator includes system 100 providing a request for establishing a referral connection to investigator system 126. Based on the received request, investigator system 126 may provide a reply communication, to provider system 120, which is responsive to the request. System 100 determines that the referral connection exists between the provider and the trial investigator at least based on information in the reply communication. Other processes for establishing a referral connection, identifying one or more providers, and/or determining whether a referral connection exists are described in more detail in related U.S. patent application Ser. No. 15/914,653 filed on Mar. 7, 2018.

System 100 provides the information about the trial program for analysis at a provider system (206). For example, system 100 provides trial program criteria for analysis at a provider system. In some implementations, a set of criteria for the trial program includes: i) inclusion criteria for identifying candidate subjects for participating in the trial program; and ii) exclusion criteria for identifying candidate subjects to be excluded from participating in the trial program. Provider system 120 is configured to access healthcare data for multiple subjects that interact with the provider. For example, the multiple subjects can be sets of patient that are treated by a provider such as a physician or related medical professional.

System 100 generates data indicating a result of screening each of the multiple subjects (208). The system generates the data based on analysis of the information about the trial program against the healthcare data accessed for each of the multiple subjects. For example, system 100 generates the data (e.g., screening data) by analyzing the trial program criteria against healthcare data for each subject. For example, the system generates screening data by digitally screening health attributes of a set of subjects or patients against inclusion and exclusion criteria. The inclusion and exclusion criteria may each specify health related requirements for determining whether a particular subject can participate in a trial program. For example, the criteria can specify a drug compound and measures for determining that a particular subject is medically cleared to use a drug compound that has a particular chemical composition or molecule. The criteria may also specify a healthcare indication or that a patient must have one or more medical conditions (e.g., a certain form or stage of lung cancer) that are being targeted for treatment using the drug compound. For example, the criteria might specify that only subjects with non-small cell lung cancer, e.g., with subtypes squamous cell carcinoma, adenocarcinoma, or large cell carcinoma, are permitted to participate in the trial program.

System 100 receives, from a provider system, data for a selection of a subject from among the multiple subjects (210). The selection can be determined or processed at the provider system 120 based on screening data generated for the subject. For example, system 100 can receive data for a selection of a subject that was digitally screened against a set of inclusion (or exclusion) criteria for a particular clinical trial. In one implementation, a clinical trial may be conducted to evaluate the efficacy of a drug compound for treating a certain type of cancer. In some cases, the selection occurs based on manual input from a user. In some cases, the selection is automatically determined based on analysis of the screening data for the subject. For example, the screening data can include parameter values indicating that the patient is a candidate (or not a candidate) for participation in the clinical trial for evaluating a drug compound for treating a new form of lung cancer.

In some implementations, receiving the data for selection of the subject from provider system 120 is preceded by: i) provider system 120 accessing, e.g., using platform 102, healthcare data for subjects that interact with a physician; ii) determining that the subject is a candidate for participation in the trial program based on analysis of data describing a first healthcare indication or a therapeutic compound referenced in the information about the trial program; and iii) providing a notification about selection of the subject in response to determining that the subject is candidate for the trial program. Determining that the subject is a candidate for participation in the trial program can include: i) identifying a second healthcare indication connected to the subject based on the data describing the personal health attributes of the subject; ii) analyzing terms describing the first and second healthcare indications to determine a match between the indications; and iii) determining that the subject is a candidate for participation in the trial program based on the determined match. In some implementations, in addition to the terms, respective parameter values for the first and second healthcare indications as well as various other trial criteria and subject heath data are analyzed to determine matches between data describing health attributes of the subject and the information about the trial program.

System 100 provides screening data for the subject for access at an investigator system (212). The screening data is provided using a digital referral network of the system and indicates or describes a screening outcome for the subject. The screening data is provided for analysis (e.g., automated analysis) at the investigator system. In some implementations, the screening data is analyzed using the investigator system and by an investigator that conducts a clinical trial. The screening data can include information describing health attributes of the subject and results of screening (e.g., digitally screening) the subject's health attributes against inclusion and/or exclusion criteria for the trial program. For example, the screening data may include de-identified information about the patient as well as the patient's age, gender, health records data identifying existing medical conditions, or a geographic location. The screening data indicates whether the subject is a suitable candidate for participation in the trial. For example, the screening data may indicate this information based on analysis of at least the subject's medical condition against criteria of the trial program that defines medical conditions that are appropriate for participation in the trial program.

Figure 3:
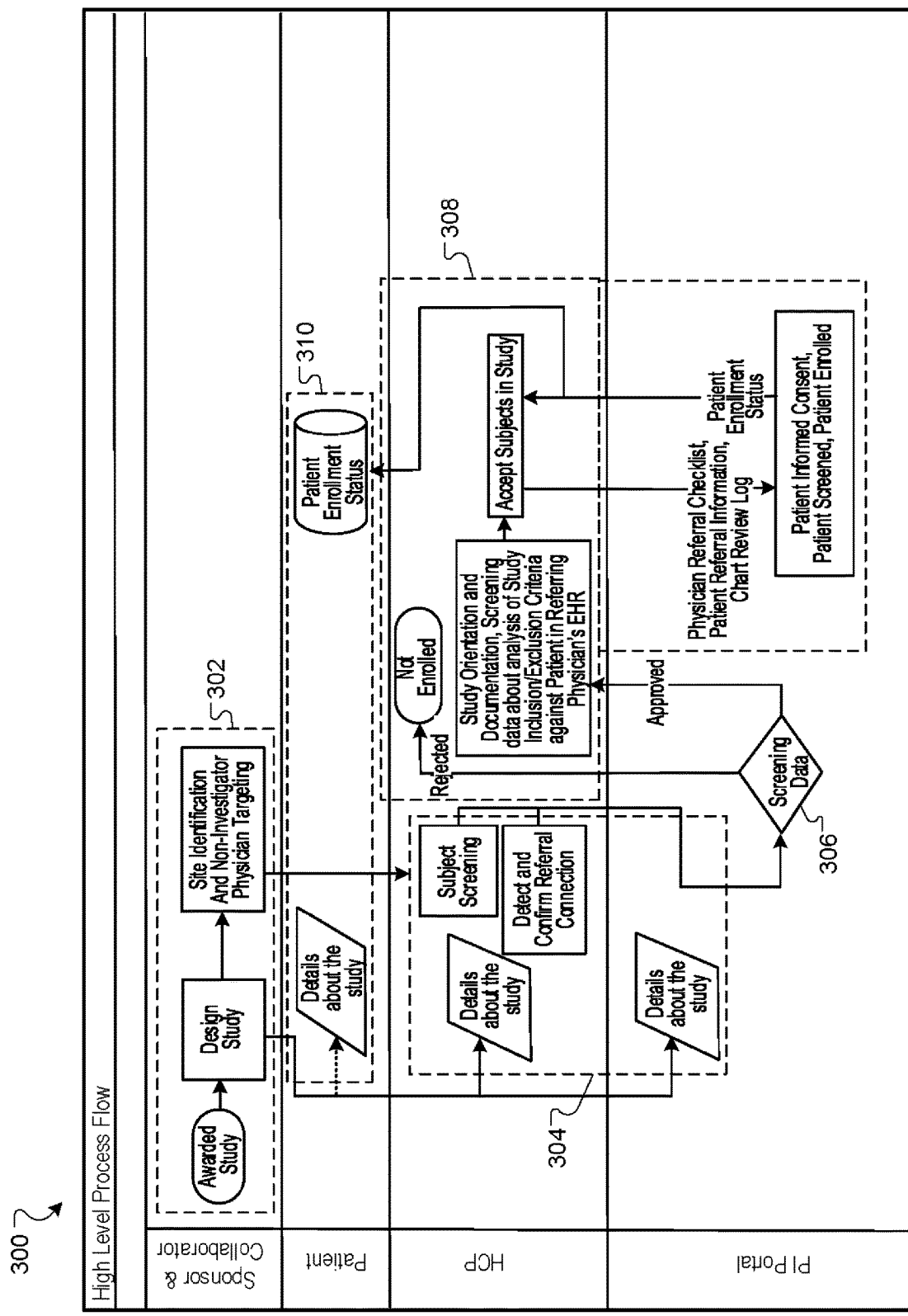
FIG. 3 shows a diagram that includes an example of information flow in a digital referral network.

FIG. 3 shows a diagram that includes an example process 200 indicating information flow in referral network 104. Similar to process 200, process 300 can be also implemented or executed using the systems described in this document. Hence, descriptions of process 300 may reference one or more of the above-mentioned computing resources of system 100 and steps of process 300 can be enabled by computing logic that is executable by processing devices and memory of the systems described in this document.

Referring now to process 300, a sponsor is awarded a study, initiates design of the study, and collaborates with an example private entity to identify or target one or more other entities (e.g., non-investigator physicians) for developing and executing different aspects of the study (302). The private entity can be an example health information technology company that owns or manages computing platform 102 and the sponsor can determine whether to use computing platform 102 as a collaboration solution for the study. In some implementations, block 302 of process 300 includes the sponsor determining that services offered by computing platform 302 will be used to execute the study. Based on this determination, computing platform 102 identifies a particular entity, e.g., a site location or non-investigator physician, and provides the identified entity to the sponsor as a candidate for executing aspects of the study. The sponsor determines whether to accept and confirm the identified entity as a target for executing one or more aspects of the study. The study can be a clinical trial or other controlled program that is executed to evaluate a drug compound for treating a particular medical condition (e.g., diabetes or high cholesterol). In some cases, the platform 102 is used in conjunction with a variety of clinical study types. For example, the study types can include clinical trials and controlled programs for evaluating drugs, devices (e.g., medical devices), and observational studies, as well as various types of virtual trials. In some implementations, targeting the one or more entities for developing and executing different aspects of the study includes accessing and analyzing information stored at datasets 108 to identify a geographic site location(s) for conducting the clinical trial, an investigator(s) for managing execution of the clinical trial, and one or more non-investigator physicians for obtaining subjects for participation in the clinical trial.

Data and other information describing various details about the clinical trial are provided to at least one investigator managing the trial and at least one healthcare physician that provides referral data to the investigator (304). In some implementations, the physician (a provider) and the investigator have a preexisting referral relationship that is enabled by a secure electronic referral connection. The secure electronic referral connection enables sensitive or confidential data to be exchanged between provider 120 and investigator system 126. System 100 accesses datasets 108 and analyzes information describing existing referral connections managed at referral network 104. System 100 detects or determines and confirms that an established referral connection exists between the provider and the investigator in response to the analysis (304).

As described above, system 100 generates screening data by analyzing trial inclusion criteria and trial exclusion criteria against healthcare data for each subject. For example, system 100 generates screening data based on data analysis performed locally at the provider system 120. In some implementations, system 100 facilitates access to a subject's EMR or EHR data that is stored at variety of health systems databases and use this information to generate the screening data. Using interface 124 and platform 102, provider system 120 can access these databases and initiate analytical scans of a subject's EMR to generate the screening data. Provider system 120 can digitally scan the different health attributes of a set of subjects against the trial criteria to generate the screening data.

For example, system 100 can execute specific computing rules to extract clinical trial criteria defining a drug molecule, types of medical conditions, and a health attributes of subjects such as a subject's age and existing medical conditions. Execution of the rules cause data model 118 to automatically analyze and compare health information in a subject's EMR to the extracted clinical trial criteria. The comparison can yield screening data outcomes that indicate whether parameter values of the subject's EMR data match parameter values of the representing the extracted trial criteria. In some implementations, the analysis and comparisons enable ML system 116 to generate learned inferences about patient subsets that are likely candidates for participation in certain clinical trials based on information health data about the patients and details about the trial.

Screening data outcomes can include a match score (e.g., "0" or "1") that can be used to determine if a subject is a candidate for participation in the clinical trial. For example, the match score can be a discrete binary value, such as a "1" indicating a subject is a match and should be selected for referral to an investigator as a trial candidate or a "0" indicating a subject's health data does not match with the trial criteria. In some implementations, system 100 uses ML system 116 to generate certain push notifications for receipt at provider system 120 (or investigator system 126). For example, system 100 generates data identifying healthcare providers that are candidates for "white glove" status based on the provider's eligible patient base and screening data for patients that is shared within referral network 104. Notifications for the white glove status identifies certain providers having a large percentage of patients with medical attributes that indicate the patients are candidates for enrollment in a particular clinical trial.

In some implementations, ML system 116 recommends that a provider be linked to a certain clinical trial based on EMR or EHR data indicating the doctor's patients have health attributes that match (e.g., substantially match) requirements for inclusion in a clinical trial. In some cases, system 100 and ML system 116 use analytics model 118 to integrate certain types of EHR data in datasets 108. In response to integrating the data, system 100 can access and analyze the data against criteria for a clinical trial to automatically initiate screening data describing results or outcomes of the analysis. System 100 can also automatically generate notifications informing a healthcare physician (e.g., during patient review) that one or multiple patients are candidates for a clinical trial.

The described techniques leverage the specific components and computing elements of system 100 to securely access, analyze, and exchange sensitive medical information based on referral connections represent an improvement in the relevant technology and industry. For example, using the described techniques entities (e.g., medical entities) are able to increase subject enrollment in clinical trials with improved efficiency over prior methods. This is because prior methods for sharing patient data for clinical trial enrollment were unable to leverage electronic referral connections due to the limitations of the relevant technology and the complexity of establishing digital referral networks in a secure and computationally efficient manner, particularly in the context of clinical trials.

System 100 provides screening data generated at a provider system to an investigator system (306). In some implementations, the screening data includes sensitive medical information that is transmitted using an encrypted or secure data channel, while in other implementations the screening data is de-identified by removing, excluding, or redacting certain types of identifying data of the patient. As discussed above, the screening data is provided through secure communication channels established by digital referral network 104 based on the referral connection that exists between the provider and the trial investigator. The screening data can include anonymized identifiers for a subject and anonymized data about personal health attributes of the subject. In some cases, the screening data is linked to electronic healthcare records and electronic healthcare transaction data about the subject. The health care records and transaction data can be derived based on the subject's interaction with the provider.

Investigator system 126 receives the data via platform 102 and presents the data for display at a graphical interface 130 that is generated using an API of portal interface 112. An investigator that is connected to a referring physician/provider approves or validates the subject's acceptance into the trial program (308). As shown at FIG. 3, acceptance of a subject as a participant in a clinical trial program can cause a variety of information and different types of data to be exchanged between provider system 120 and investigator system 126. The data and information are exchanged using interfaces 124, 130 generated via platform 102.

System 100 provides data communications to a subject using interface 134. The data communications may inform the subject of their acceptance in a clinical trial when a provider has referred the subject to an investigator (310). In some implementations, a subject can receive a message communication at interface 134 that includes an electronic invitation to self-enroll for participation in a clinical trial. For example, system 100 can generate the message communication based on screening data outcomes that include a match score (e.g., binary "1") which indicates the subject is a candidate for participation in a certain trial.

Figure 4:
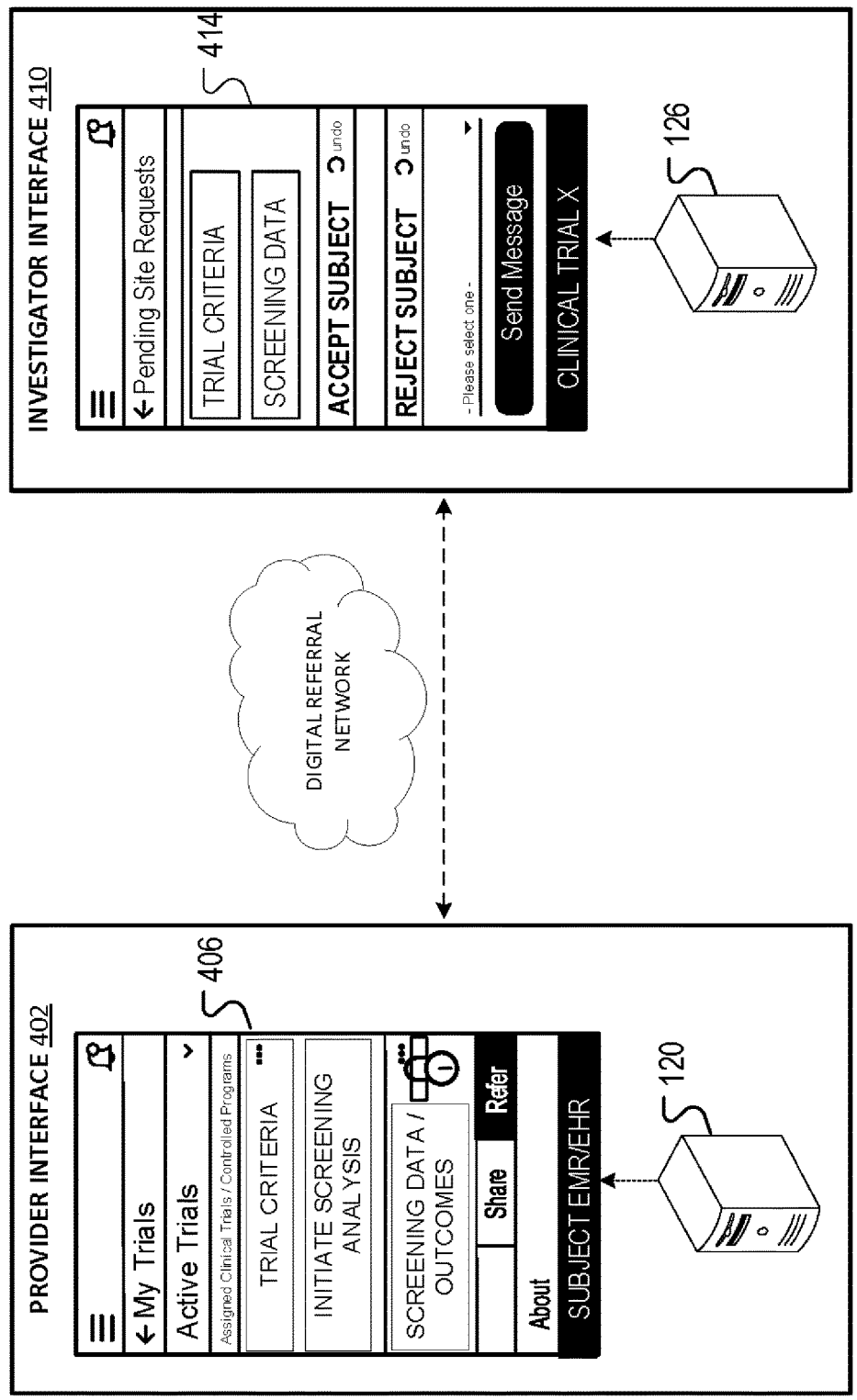
FIG. 4 shows graphical user interfaces that are generated using an application program of a digital referral network.

FIG. 4 shows graphical user interfaces that are generated using an application program managed at platform 102. Healthcare provider interface 402 corresponds to interface 124 described above with reference to FIG. 1, while investigator interface 410 corresponds to investigator interface 130 also described above with reference to FIG. 1. As shown at FIG. 4, interface 402 can include different graphical data 406. Similarly, interface 410 can include different graphical data 414. Data 406 includes information about inclusion and exclusion criteria for an example clinical trial. Data 406 can also include an input selection for initiating screening analysis for analyzing health attributes for a subject against requirements defined in the trial criteria. Graphical data displayed at interface 410 can also include information describing screening data outcomes generated in response to initiating the screening analysis. Data 414 can also include respective input selections for accepting or rejection a subject for participation in a clinical trial based on the information describing screening data outcomes generated in response to initiating the screening analysis.

Figure 5:
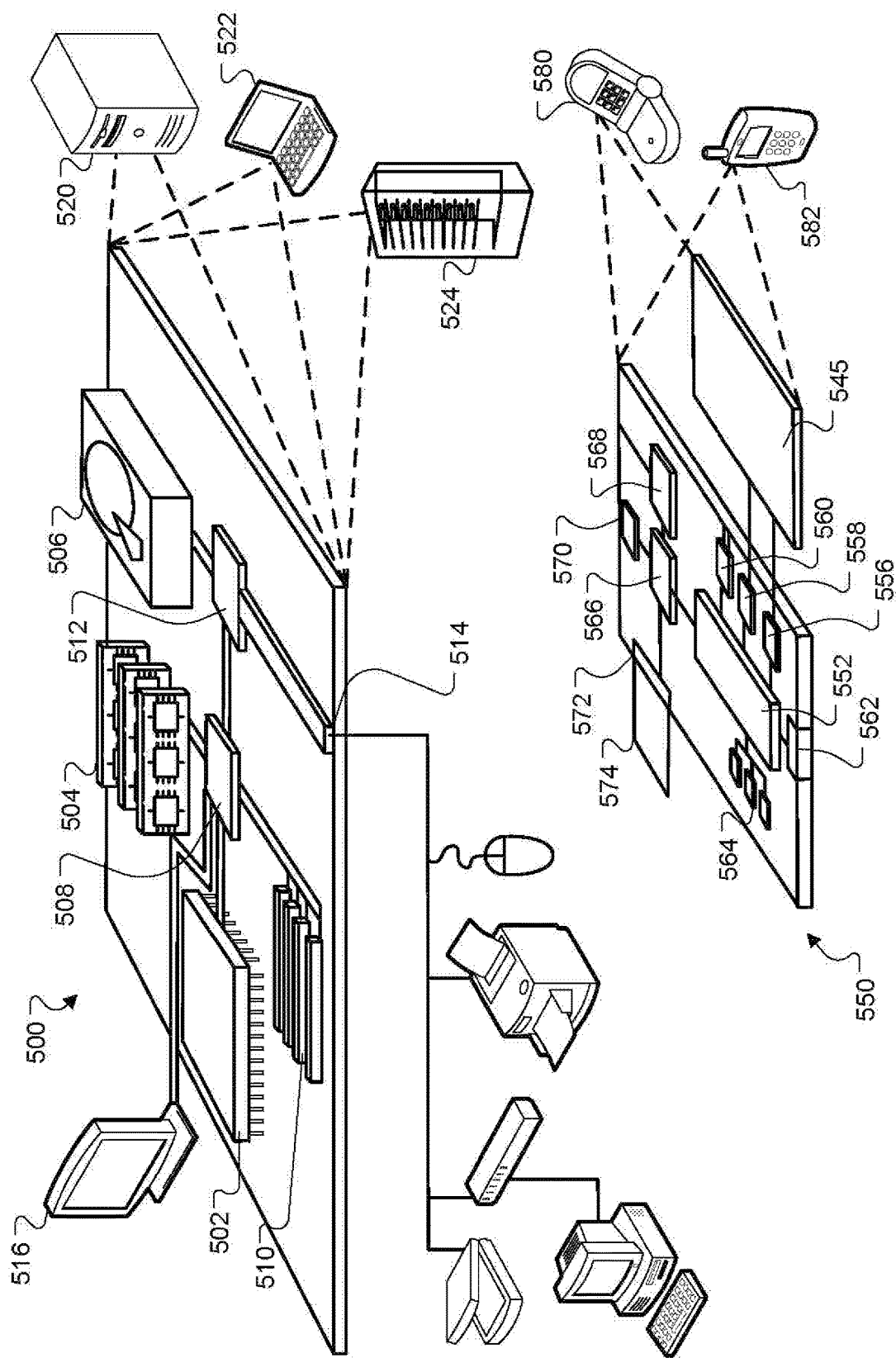
FIG. 5 shows a block diagram of a computing system that can be used in connection with computer-implemented methods described in this specification.

FIG. 5 is a block diagram of computing devices 500, 550 that may be used to implement the systems and methods described in this document, as either a client or as a server or plurality of servers. Computing device 500 is intended to represent various forms of digital computers, such as laptops, desktops, workstations, personal digital assistants, servers, blade servers, mainframes, and other appropriate computers. In some implementations, computing device 500 is a cloud-based computer system that facilitates connections and communications between the various entities (e.g., providers and investigators) and the participants, patients, or subjects described in this document. For example, computing device 500 facilitates the exchange of data communications between provider system 120, investigator system 126, and patient device 132. In general, computing device 500 can be a cloud computer system used to implement the different computing functions of platform 102 that are described herein.

Computing device 550 can represent various forms of mobile devices, such as personal digital assistants, cellular telephones, smartphones, smartwatches, head-worn devices, and other similar computing devices. The components shown here, their connections and relationships, and their functions, are meant to be exemplary only, and are not meant to limit implementations described and/or claimed in this document.

Computing device 500 includes a processor 502, memory 504, a storage device 506, a high-speed interface 508 connecting to memory 504 and high-speed expansion ports 510, and a low speed interface 512 connecting to low speed bus 514 and storage device 506. Each of the components 502, 504, 506, 508, 510, and 512, are interconnected using various busses, and may be mounted on a common motherboard or in other manners as appropriate. The processor 502 can process instructions for execution within the computing device 500, including instructions stored in the memory 504 or on the storage device 506 to display graphical information for a GUI on an external input/output device, such as display 516 coupled to high speed interface 508. In other implementations, multiple processors and/or multiple buses may be used, as appropriate, along with multiple memories and types of memory. Also, multiple computing devices 500 may be connected, with each device providing portions of the necessary operations, e.g., as a server bank, a group of blade servers, or a multi-processor system.

The memory 504 stores information within the computing device 500. In one implementation, the memory 504 is a computer-readable medium. In one implementation, the memory 504 is a volatile memory unit or units. In another implementation, the memory 504 is a non-volatile memory unit or units.

The storage device 506 is capable of providing mass storage for the computing device 500. In one implementation, the storage device 506 is a computer-readable medium. In various different implementations, the storage device 506 may be a floppy disk device, a hard disk device, an optical disk device, or a tape device, a flash memory or other similar solid state memory device, or an array of devices, including devices in a storage area network or other configurations. In one implementation, a computer program product is tangibly embodied in an information carrier. The computer program product contains instructions that, when executed, perform one or more methods, such as those described above. The information carrier is a computer- or machine-readable medium, such as the memory 504, the storage device 506, or memory on processor 502.

The high speed controller 508 manages bandwidth-intensive operations for the computing device 500, while the low speed controller 512 manages lower bandwidth-intensive operations. Such allocation of duties is exemplary only. In one implementation, the high-speed controller 508 is coupled to memory 504, display 516, e.g., through a graphics processor or accelerator, and to high-speed expansion ports 510, which may accept various expansion cards (not shown). In the implementation, low-speed controller 512 is coupled to storage device 506 and low-speed expansion port 514. The low-speed expansion port, which may include various communication ports, e.g., USB, Bluetooth, Ethernet, wireless Ethernet, may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. It may also be implemented as part of a rack server system 524. In addition, it may be implemented in a personal computer such as a laptop computer 522. Alternatively, components from computing device 500 may be combined with other components in a mobile device (not shown), such as device 550. Each of such devices may contain one or more of computing device 500, 550, and an entire system may be made up of multiple computing devices 500, 550 communicating with each other.

Computing device 550 includes a processor 552, memory 564, an input/output device such as a display 554, a communication interface 566, and a transceiver 568, among other components. The device 550 may also be provided with a storage device, such as a microdrive or other device, to provide additional storage. Each of the components 550, 552, 564, 554, 566, and 568, are interconnected using various buses, and several of the components may be mounted on a common motherboard or in other manners as appropriate.

The processor 552 can process instructions for execution within the computing device 550, including instructions stored in the memory 564. The processor may also include separate analog and digital processors. The processor may provide, for example, for coordination of the other components of the device 550, such as control of user interfaces, applications run by device 550, and wireless communication by device 550.

Processor 552 may communicate with a user through control interface 558 and display interface 556 coupled to a display 554. The display 554 may be, for example, a TFT LCD display or an OLED display, or other appropriate display technology. The display interface 556 may include appropriate circuitry for driving the display 554 to present graphical and other information to a user. The control interface 558 may receive commands from a user and convert them for submission to the processor 552. In addition, an external interface 562 may be provided in communication with processor 552, so as to enable near area communication of device 550 with other devices. External interface 562 may provide, for example, for wired communication, e.g., via a docking procedure, or for wireless communication, e.g., via Bluetooth or other such technologies.

The memory 564 stores information within the computing device 550. In one implementation, the memory 564 is a computer-readable medium. In one implementation, the memory 564 is a volatile memory unit or units. In another implementation, the memory 564 is a non-volatile memory unit or units. Expansion memory 574 may also be provided and connected to device 550 through expansion interface 572, which may include, for example, a SIMM card interface. Such expansion memory 574 may provide extra storage space for device 550, or may also store applications or other information for device 550. Specifically, expansion memory 574 may include instructions to carry out or supplement the processes described above, and may include secure information also. Thus, for example, expansion memory 574 may be provided as a security module for device 550, and may be programmed with instructions that permit secure use of device 550. In addition, secure applications may be provided via the SIMM cards, along with additional information, such as placing identifying information on the SIMM card in a non-hackable manner.

The memory may include for example, flash memory and/or MRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 564, expansion memory 574, or memory on processor 552.

Device 550 may communicate wirelessly through communication interface 566, which may include digital signal processing circuitry where necessary. Communication interface 566 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 568. In addition, short-range communication may occur, such as using a Bluetooth, WiFi, or other such transceiver (not shown). In addition, GPS receiver module 570 may provide additional wireless data to device 550, which may be used as appropriate by applications running on device 550.

Device 550 may also communicate audibly using audio codec 560, which may receive spoken information from a user and convert it to usable digital information. Audio codec 560 may likewise generate audible sound for a user, such as through a speaker, e.g., in a handset of device 550. Such sound may include sound from voice telephone calls, may include recorded sound, e.g., voice messages, music files, etc., and may also include sound generated by applications operating on device 550.

The computing device 550 may be implemented in a number of different forms, as shown in the figure. For example, it may be implemented as a cellular telephone 580. It may also be implemented as part of a smartphone 582, personal digital assistant, or other similar mobile device.

Various implementations of the systems and techniques described here can be realized in digital electronic circuitry, integrated circuitry, specially designed ASICs, computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs, also known as programs, software, software applications or code, include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back-end component, e.g., as a data server, or that includes a middleware component such as an application server, or that includes a front-end component such as a client computer having a graphical user interface or a Web browser through which a user can interact with an implementation of the systems and techniques described here, or any combination of such back-end, middleware, or front-end components. The components of the system can be interconnected by any form or medium of digital data communication such as, a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In addition, certain data may be treated in one or more ways before it is stored or used, so that personally identifiable information is removed. For example, in some embodiments, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over what information is collected about the user, how that information is used, and what information is provided to the user.

A number of embodiments have been described. Nevertheless, it will be understood that various modifications may be made without departing from the spirit and scope of the invention. Accordingly, other embodiments are within the scope of the following claims. While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment.

Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, some processes depicted in the accompanying figures do not necessarily require the particular order shown, or sequential order, to achieve desirable results.

The invention claimed is:

1. A computer-implemented method, comprising:
    identifying criteria for participation in a trial program by one or more subjects;
    generating an analytics model based on inferences learned from iterative analysis of a dataset comprising different clinical trial criteria and healthcare transaction data;
    using the analytics model to model connections between: (i) data describing healthcare activity of a plurality of subjects, (ii) data about a physician that administers treatment relating to the healthcare activity, and (iii) the criteria for participation in the trial program;
    based on the connections, digitally screening, using the analytics model, anonymized healthcare data for each of the plurality of subjects against the criteria for participation in the trial program;
    generating, using the analytics model, screening data for each of the plurality of subjects that indicates a respective result of the digital screening, wherein the result includes a respective match score that indicates whether a corresponding one of the plurality of subjects satisfies the criteria for participation in the trial program;
    selecting a subject from among the plurality of subjects based on the respective match score for the subject indicating the subject satisfies the criteria for participation in the trial program; and
    providing, using a digital referral network, the screening data for the subject that was selected to an investigator of the trial program based on a referral connection that exists between the provider and the investigator in the digital referral network.

2. The method of claim 1, wherein the screening data is provided through communication channels enabled by the digital referral network based on the referral connection that exists between the provider and the investigator.

3. The method of claim 1, wherein:
the screening data comprises an anonymized identifier for the subject that was selected and data describing personal health attributes of the subject; and
the method comprises:
linking the screening data to electronic healthcare records and electronic healthcare transaction data about the subject that are derived for the subject based on the provider having interacted with the subject during a healthcare transaction.

4. The method of claim 3, wherein the method comprises:
identifying each of the plurality of subjects as a prospective candidate for participation in the trial program based on the respective match score for each subject indicating the subject satisfies the criteria for participation in the trial program.

5. The method of claim 4, wherein the criteria includes inclusion criteria and exclusion criteria, and the method further comprises:
processing, using the analytics model, each of the inclusion criteria and the exclusion criteria against anonymized information obtained from electronic healthcare records of the subject or electronic healthcare transaction data about the subject;
generating, using the analytics model, the respective match score for the subject in response to processing each of the inclusion criteria and the exclusion criteria against the anonymized information obtained from the electronic healthcare records of the subject or the electronic healthcare transaction data about the subject; and
determining, using the analytics model, that the subject is a prospective candidate for participation in the trial program based on the respective match score exceeding a threshold match score.

6. The method of claim 4, wherein the method comprises:
accessing healthcare data for the plurality of subjects that interact with the provider;
determining, by the analytics models, that the subject that was selected is a candidate for participation in the trial program based on analysis of data describing a first healthcare indication or a therapeutic compound referenced in the criteria; and
in response to determining that the subject is a candidate for participation in the trial program, providing, for receipt at a system of the digital referral network, a notification that indicates selection of the subject for the trial program.

7. The method of claim 6, wherein determining that the subject is a candidate for participation in the trial program comprises:
identifying a second healthcare indication connected to the subject based on the data describing the personal health attributes of the subject;
determining a match between the first healthcare indication and the second healthcare indication based on analysis of terms that describe each of the first and second healthcare indications; and
based on the determined match, determining that the subject is a candidate for participation in the trial program.

8. The method of claim 6, wherein determining that the subject is a candidate for participation in the trial program comprises:
determining that the subject is a candidate for participation in the trial program based on a screening outcome derived from the screening data.

9. The method of claim 1, wherein:
a screening outcome derived from the screening data indicates that the subject passed a pre-screening analysis based on results of an analytical sequence executed using the analytical model; or
a screening outcome derived from the screening data indicates that the subject failed a pre-screening analysis based on results of an analytical sequence executed using the analytical model.

10. The method of claim 1, wherein providing the screening data for the subject that was selected to an investigator of the trial program comprises:
determining that a referral connection exists between the provider and the trial investigator; and
providing the screening data for the subject based on the referral connection enabling a computer system managed by the investigator to receive the screening data from a system of the digital referral network.

11. The method of claim 10, wherein determining that the referral connection exists between the provider and the trial investigator comprises:
providing, by a provider system and atoll the computer system managed by the investigator, a request to establish the referral connection;
providing, by the computer system managed by the investigator and to the provider system, reply communication that is responsive to the request; and
determining that the referral connection exists between the provider and the trial investigator based on information in the reply communication.

12. A system, comprising one or more processing devices; and one or more non-transitory machine-readable storage devices storing instructions that are executable by the one or more processing devices to cause performance of operations comprising:
identifying criteria for participation in a trial program by one or more subjects;
generating an analytics model based on inferences learned from iterative analysis of a dataset comprising different clinical trial criteria and healthcare transaction data;
using the analytics model to model connections between: (i) data describing healthcare activity of a plurality of subjects, (ii) data about a physician that administers treatment relating to the healthcare activity, and (iii) the criteria for participation in the trial program;
based on the connections, digitally screening, using the analytics model, anonymized healthcare data for each of the plurality of subjects against the criteria for participation in the trial program;
generating, using the analytics model, screening data for each of the plurality of subjects that indicates a respective result of the digital screening, wherein the result includes a respective match score that indicates whether a corresponding one of the plurality of subjects satisfies the criteria for participation in the trial program;
selecting a subject from among the plurality of subjects based on the respective match score for the subject indicating the subject satisfies the criteria for participation in the trial program; and
providing, using a digital referral network, the screening data for the subject that was selected to an investigator of the trial program based on a referral connection that exists between the provider and the investigator in the digital referral network.

13. The system of claim 12, wherein the screening data is provided through communication channels enabled by the digital referral network based on the referral connection that exists between the provider and the investigator.

14. The system of claim 12, wherein:
the screening data comprises an anonymized identifier for the subject that was selected and data describing personal health attributes of the subject; and
the operations comprise:
linking the screening data electronic healthcare records and electronic healthcare transaction data about the subject that are derived for the subject based on the provider having interacted with the subject during a healthcare transaction.

15. The system of claim 14, wherein the operations comprise:
identifying each of the plurality of subjects as a prospective candidate for participation in the trial program based on the respective match score for each subject indicating the subject satisfies the criteria for participation in the trial program.

16. The system of claim 15, wherein the criteria includes inclusion criteria and exclusion criteria, and the operations further comprise:
processing, using the analytics model, each of the inclusion criteria and the exclusion criteria against anonymized information obtained from electronic healthcare records of subject or the electronic healthcare transaction data about the subject;
generating, using the analytics model, the respective match score for the subject in response to processing each of the inclusion criteria and the exclusion criteria against the anonymized information obtained from the electronic healthcare records of the subject or the electronic healthcare transaction data about the subject; and
determining, using the analytics model, that the subject is a prospective candidate for participation in the trial program based on the respective match score exceeding a threshold match score.

17. The system of claim 15, wherein the operations comprise:
accessing healthcare data for the plurality of subjects that interact with the provider;
determining, by the analytics models, that the subject that was selected is a candidate for participation in the trial program based on analysis of data describing a first healthcare indication or a therapeutic compound referenced in the criteria; and
in response to determining that the subject is a candidate for participation in the trial program, providing, for receipt at a system of the digital referral network, a notification that indicates selection of the subject for the trial program.

18. The system of claim 17, wherein determining that the subject is a candidate for participation in the trial program comprises:
identifying a second healthcare indication connected to the subject based on the data describing the personal health attributes of the subject;
determining a match between the first healthcare indication and the second healthcare indication based on analysis of terms that describe each of the first and second healthcare indications; and
based on the determined match, determining that the subject is a candidate for participation in the trial program.

19. The system of claim 17, wherein determining that the subject is a candidate for participation in the trial program comprises:
determining that the subject is a candidate for participation in the trial program based on a screening outcome derived from the screening data.

20. One or more non-transitory machine-readable storage devices storing instructions that are executable by one or more processing devices to cause performance of operations comprising:
identifying criteria for participation in a trial program by one or more subjects;
generating an analytics model based on inferences learned from iterative analysis of a dataset comprising different clinical trial criteria and healthcare transaction data;
using the analytics model to model connections between: (i) data describing healthcare activity of a plurality of subjects, (ii) data about a physician that administers treatment relating to the healthcare activity, and (iii) the criteria for participation in the trial program;
based on the connections, digitally screening, using the analytics model, anonymized healthcare data for each of the plurality of subjects against the criteria for participation in the trial program;
generating, using the analytics model, screening data for each of the plurality of subjects that indicates a respective result of the digital screening, wherein the result includes a respective match score that indicates whether a corresponding one of the plurality of subjects satisfies the criteria for participation in the trial program;
selecting a subject from among the plurality of subjects based on the respective match score for the subject indicating the subject satisfies the criteria for participation in the trial program; and
providing, using a digital referral network, the screening data for the subject that was selected to an investigator of the trial program based on a referral connection that exists between the provider and the investigator in the digital referral network.

* * * * *

UNITED STATES PATENT AND TRADEMARK OFFICE
CERTIFICATE OF CORRECTION

PATENT NO. : 10,978,180 B1  
APPLICATION NO. : 16/048845  
DATED : April 13, 2021  
INVENTOR(S) : Katie Shaw et al.

Page 1 of 1

It is certified that error appears in the above-identified patent and that said Letters Patent is hereby corrected as shown below:

In the Claims

Column 20, Line 22, Claim 11, after "and" delete "atoll" and insert -- to --.

Column 21, Line 8, Claim 14, after "data" insert -- to --.

Column 21, Line 27, Claim 16, before "subject" insert -- the --;

Column 21, Line 27, Claim 16, before "electronic" delete "the".

Signed and Sealed this  
Thirteenth Day of July, 2021

Drew Hirshfeld  
*Performing the Functions and Duties of the*  
*Under Secretary of Commerce for Intellectual Property and*  
*Director of the United States Patent and Trademark Office*